(12) United States Patent
Allier

(10) Patent No.: US 8,605,265 B2
(45) Date of Patent: Dec. 10, 2013

(54) OPTICAL DETECTION PROCESS FOR DETECTING MICRON-SIZED OBJECTS IN SOLUTION

(75) Inventor: Cédric Allier, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 307 days.

(21) Appl. No.: 12/994,460

(22) PCT Filed: Oct. 14, 2010

(86) PCT No.: PCT/EP2010/065382
§ 371 (c)(1),
(2), (4) Date: Nov. 24, 2010

(87) PCT Pub. No.: WO2011/045360
PCT Pub. Date: Apr. 21, 2011

(65) Prior Publication Data
US 2011/0228256 A1 Sep. 22, 2011

(51) Int. Cl.
*G01N 1/00* (2006.01)
(52) U.S. Cl.
USPC .......................................................... 356/36
(58) Field of Classification Search
USPC .......................................................... 356/36
See application file for complete search history.

(56) References Cited

U.S. PATENT DOCUMENTS

| | | | |
|---|---|---|---|
| 6,312,960 B1 * | 11/2001 | Balch et al. | 506/32 |
| 7,201,878 B2 * | 4/2007 | Lin et al. | 422/88 |
| 2002/0198928 A1 | 12/2002 | Bukshpan et al. | |
| 2007/0273867 A1 | 11/2007 | Diessel et al. | |
| 2012/0021932 A1 * | 1/2012 | Mershin et al. | 506/9 |
| 2012/0224053 A1 * | 9/2012 | Vykoukal et al. | 348/135 |

FOREIGN PATENT DOCUMENTS

| | | |
|---|---|---|
| FR | 2192708 | 2/1974 |
| FR | 2887983 | 1/2007 |
| WO | 2007131945 | 11/2007 |

OTHER PUBLICATIONS

Jung et al., "Behavior of Particles in an Evaporating Didisperse Colloid Droplet on a Hydrophilic Surface," Anal. Chem., vol. 81, No. 1, pp. 8256-8259 (Oct. 1, 2009).*
R.M. Marino, et al., "Jigsaw: A Foliage-Penetrating 3D Imaging Laser Radar System," Lincoln Laboratory Journal, vol. 15, No. 1, 2005, pp. 23-36.
Nelliimoottili et al., "Evaporation-Induced Patterns from Droplets Containing Motile and Non-Motile Bacteria," Langmuir (Amer. Chem. Soc.), vol. 23, No. 17, pp. 8655-8658 (Dec. 7, 2007).
Seo et al., "Lensfree Holographic Imaging for On-Chip Cytometry and Diagnostic," Lab Chip (Royal Chem. Soc.), vol. 9, pp. 777-787 (Dec. 5, 2008).
Klupsch et al., "The Distribution of a Macromolecular Solute Within an Evaporating Drop: An Exact Analytical Solution," Colloid and Surfaces, vol. 231, pp. 85-102 (Dec. 12, 2003).

* cited by examiner

*Primary Examiner* — Roy M Punnoose
(74) *Attorney, Agent, or Firm* — Baker & Hostetler LLP

(57) ABSTRACT

An optical detection process relates to detecting micron- or submicron-sized particles or organisms by means of a contact imaging device, the particles or organisms being immersed in a liquid droplet and the detection being carried out by means of a matrix of photosensitive cells or photosites. The process includes one detection step or a succession of detection steps carried out while the liquid droplet is evaporating. The process may also include a detection step carried out after the liquid droplet has evaporated. The process allows a three-dimensional distribution of the particles or organisms in the initial unevaporated droplet to be reconstructed.

14 Claims, 6 Drawing Sheets

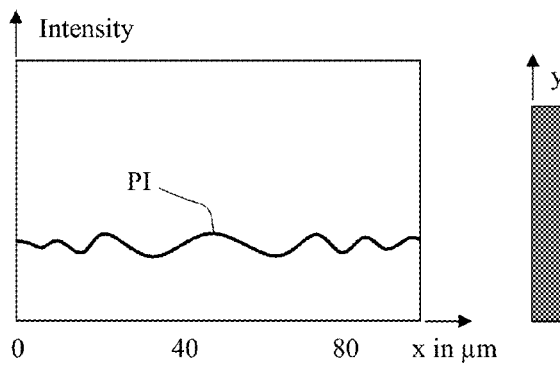
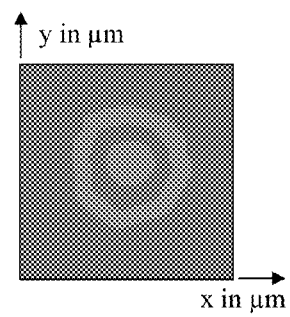
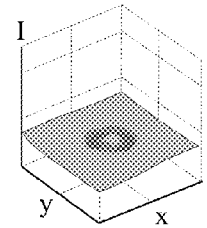
FIG. 6a　　　　FIG. 6b　　　FIG. 6c
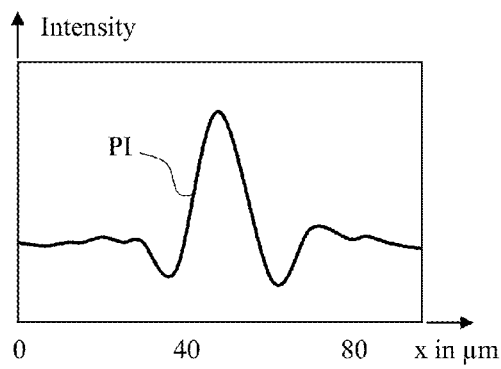
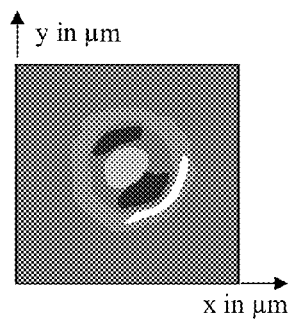
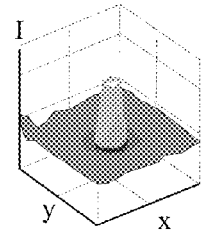
FIG. 6d　　　　FIG. 6e　　　FIG. 6f

OPTICAL DETECTION PROCESS FOR DETECTING MICRON-SIZED OBJECTS IN SOLUTION

CROSS-REFERENCE TO RELATED APPLICATIONS

This application is a National Stage of International patent application PCT/EP2010/065382, filed on Oct. 14, 2010, which claims priority to foreign French patent application No. FR 09 04966, filed on Oct. 16, 2009, the disclosures of which are incorporated by reference in their entirety.

FIELD OF THE INVENTION

The field of the invention is that of contact imaging devices and detection processes for biological diagnostics and analysis.

BACKGROUND OF THE INVENTION

In the field of optical imaging for biological diagnostics, if specific detection other than contact imaging is focused on, two methods are commonly used. These methods are flow cytometry and fluorescence molecular imaging.

Flow cytometry is a powerful technique that counts, characterizes and sorts the various cells that cut the light beam of a laser. By analyzing the diffraction patterns created it is possible to determine the dimensions of the cells. Fluorescence measurements furthermore allow the various families of bacteria to be distinguished. The drawback of this technique is that it requires expensive and complicated equipment. Another drawback is that the solid angle scanned is relatively small, limiting the field that can be investigated.

Fluorescence molecular imaging is a method widely used in biological diagnostics because it is extremely effective. Fluorescence measurements are sensitive to single events: using fluorescent labels it is possible to detect individual molecules using a microscope. To obtain good results it is necessary to completely separate the energy for exciting the fluorescent molecules—called the "excitation" energy—from the energy emitted by the fluorescent molecules—called the "emission" energy. Although excellent filters exist at the present time, they constrain the light beams, in particular requiring them to have small beam-apertures. Consequently, the optical systems that this method uses are complicated and bulky. Fluorescence imaging also requires prior addition of a fluorophore to the medium to be analyzed, making the process invasive.

Thus, it is desired to replace these complicated and costly techniques with noninvasive contact imaging devices having extended fields of observation.

These techniques are being developed further and further because they allow cells, bacteria or more generally micron-sized particles to be detected without requiring the aforementioned advanced optical systems. A schematic of a contact imaging device is shown in FIG. 1. This device comprises a light source 1, possibly a small source, for example a light-emitting diode, a diaphragm 2 limiting the aperture of the source and an imager or sensor 3, which may be a matrix of CCD (charge-coupled device) or CMOS (complementary metal oxide semiconductor) photosites. Such imagers generally comprise microlenses associated with each photosite. The diaphragm 2 is not essential, but its presence is advantageous. Inserted between this matrix 3 and the light source 1 is a transparent microscope slide 4 that carries the object 5 to be studied.

This object is a solution containing micron-sized particles—these particles may be biological particles such as cells or bacteria or other particles such as microspheres. The droplet analyzed rests on the transparent slide 4 and its meniscus is in contact with the ambient gas, which gas may be air. The matrix 3 is connected to an image display and/or processing system, not shown in FIG. 1. The distance separating the diode 1 from the object-carrying slide 4 is preferably greater than 1 cm and may be, for example, a few cm, typically between 2 cm and 5 cm. The distance separating the object from the surface of the sensor is between 0.1 mm and 2 mm. Although this is referred to as contact imaging, the object to be studied is not placed in direct contact with the sensor but at the distance indicated above. The slide is made of a transparent material such as silica or quartz and its thickness varies between a few tens of microns and 1 mm. This very simple device, without magnifying optics, may, in certain cases, be an alternative to the conventional optical counting methods such as flow cytometry, high-resolution optical microscopy or fluorescence molecular imaging.

Over the last few years, several teams have obtained impressive results using contact imaging. Thus, a team based at the American university UCLA (University of California, Los Angeles) used contact imaging to detect and identify bacteria. This method is described in the following publication: "Lensfree holographic imaging for on-chip cytometry and diagnostics" by Sungkyu Seo et al., The Royal Society of Chemistry, Dec. 5, 2008-2009, 9, 777-787. In the devices described in that publication, the bacteria are placed in a liquid between two plates, the assembly being put on a matrix of photosites. A monochromatic illumination source is filtered by a 100-µm diameter diaphragm so as to obtain good spatial coherence. Thus, at the matrix of photosites, a diffraction pattern is obtained for each immersed cell. According to the authors, the diffraction patterns obtained are sufficiently well-resolved and distinct from one species to another that specific counting of the various bacteria is possible.

The method proposed by the UCLA team is elegant. However, it has a drawback—it requires the use of high-sensitivity CCD sensors that are necessarily costly. Thus, the sensors used were Kodak Kai-10002 high-sensitivity CCD sensors.

If standard sensors, such as low-cost CMOS or CCD sensors, are used, it is still possible to observe the diffraction patterns of the various 1 µm diameter micron-sized particles such as silanol microspheres, latex microspheres or E. Coli bacteria. However, the detection efficiency is very low, at best about 1%. Thus, FIG. 2 shows the signal S obtained along an axis x of the sensor that passes through the center of a particle P. The signal S shows here the gray level along the ordinate axis measured by various pixels, the pixels forming the abscissa axis, i.e. FIG. 2 shows a profile. It may be seen that the signal-to-noise ratio is very low, barely sufficient to allow the particle to be detected.

SUMMARY OF THE INVENTION

The process according to the invention does not have these drawbacks. It in fact allows micron-sized particles to be detected using a contact imaging device without requiring high-sensitivity sensors. The main feature of the process according to the invention is to take the measurement or measurements while the liquid droplet, in which the micron-sized particles (bacteria, cells, microspheres, etc.) to be detected are found, is evaporating, or after said droplet has evaporated. Thus, unlike the measurements of the prior art, the droplet is not placed between two plates. In addition, the droplet must be in contact with a gas, for example air, so that it can evaporate. This is because it has been observed that detection is very effective during or following evaporation.

More precisely, the subject of the invention is an optical detection process for detecting micron- or submicron-sized particles or organisms by means of a contact imaging device, said particles or organisms being immersed in a liquid droplet and the detection being carried out by means of a matrix of photosensitive cells or photosites, characterized in that said process comprises at least one first detection step carried out while the liquid droplet is evaporating. The droplet may be placed either on a slide located in contact with or at a short distance from the imager or directly on the imager.

Advantageously, said process comprises at least one second detection step carried out after the droplet has evaporated.

Advantageously, detection is carried out on the periphery of the droplet, at the interface separating the droplet from its evaporated part.

Advantageously, said process comprises a succession of detection steps carried out at regular time intervals while the droplet is evaporating and/or after the droplet has evaporated, each detection step allowing the distribution of particles or organisms found in a given plane to be measured, said plane being at a distance from the matrix of photosites that depends on the evaporation time, the combination of said distributions of particles or organisms obtained allowing a three-dimensional distribution of the particles or organisms in the initial unevaporated droplet to be reconstructed.

Advantageously, the liquid is water or, when the particles to be detected are bacteria, a biological buffer, for example "Tris", the abbreviation of tris(hydroxymethyl)aminomethane. According to a preferred embodiment, the liquid comprises a wetting agent, for example Tween 20 [i.e. polyoxyethylene (20) sorbitan monolaurate].

Finally, the liquid droplet holder, either the transparent slide or the surface of the sensor, may be functionalized. It may also be made hydrophilic. It may also be cooled to below ambient temperature.

BRIEF DESCRIPTION OF THE DRAWINGS

The invention will be better understood and other advantages will become clear on reading the following description, given by way of nonlimiting example, and by virtue of the appended figures in which:

FIG. 6 shows illustrations representing observations of bacteria in a saline buffer droplet and in a film resulting from the evaporation of the droplet. The profiles (FIGS. 6a and 6d) show the detected intensity as a function of the position along a horizontal axis x;

DETAILED DESCRIPTION

Figure 3:
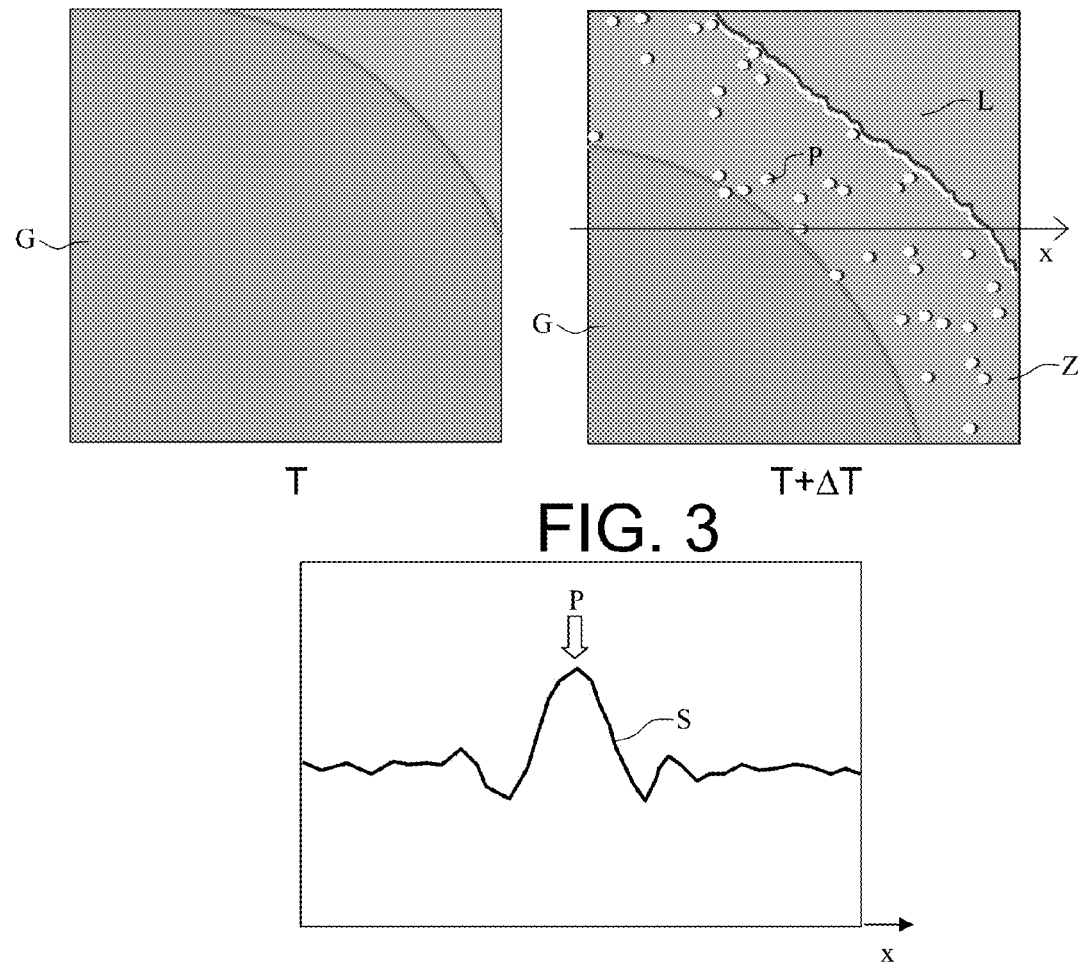
FIG. 3 shows the principle of the detection process according to the invention.

As was seen above, using a low-sensitivity sensor does not allow high signal-to-noise ratios to be obtained. The process according to the invention allows the signal-to-noise ratio, and consequently the detection efficiency, to be considerably increased. Detection systems according to the prior art detect microparticles or microorganisms within a liquid droplet. However, when the particles are immersed they are hard to detect, unless a high-sensitivity sensor is used. Thus, the view on the left of FIG. 3 shows, at a time T, the image of part of a droplet G containing particles P. The sensor of a contact imaging device as described above was used to take this image. The particles are not discernable if the sensitivity of the sensor is too low.

However, when the liquid droplet evaporates the particles, bacteria or microspheres appear very clearly at the air-liquid interface, more particularly when the particle is in the meniscus of the droplet. Thus, the view on the right of FIG. 3 shows, at a time T+ΔT, the image of part of the aforementioned droplet G after it has partially evaporated. The particles P appear clearly in the region Z of the droplet that has evaporated. The part located in the top right-hand corner, referenced with the letter L, corresponds to the part of the slide that initially was not covered by the solution.

Figure 4:
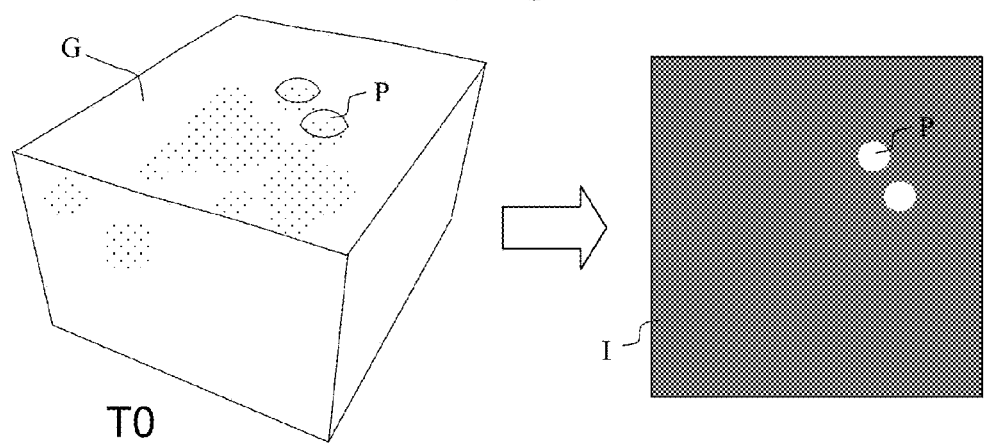
FIG. 4 shows a detection signal obtained with a low-sensitivity photosite matrix using the process according to the invention.

FIG. 4 thus shows the profile of the signal S obtained along an axis x of the sensor that passes through the center of a particle P. It is seen that the signal-to-noise ratio is now high enough to allow the particle to be detected. The signal-to-noise ratio is high enough that detection of most of the immersed cells may be envisaged—it is about a few tens of a %. This method is reproducible. The process according to the invention is therefore very simple to implement. It consists essentially in taking measurements while the liquid droplet evaporates. One measurement or detection step consists essentially in recording the signals detected by the photosites of the imager of the contact imaging device and analyzing their amplitude.

The physical explanation for this increased contrast between illuminated particles during evaporation is complicated. As is shown in the following description of experimental examples this increase may be attributed to the formation of a thin residual film that covers the particle, this film remaining for some time after the droplet has evaporated. Depending on the wettability properties of the liquid forming the droplet on the slide supporting the droplet, either this film is short-lived and disappears in a few seconds or even less, or this film is durable and remains for several seconds, even a few tens of seconds or minutes. It seems that this residual film covering the particle acts as a microlens and thus allows bacteria to be detected with a surprisingly high signal-to-noise ratio. The intensity of the signal is in fact maximized when the particle is on the evaporation line and triples when the particle is in the meniscus of the droplet.

Figure 5:
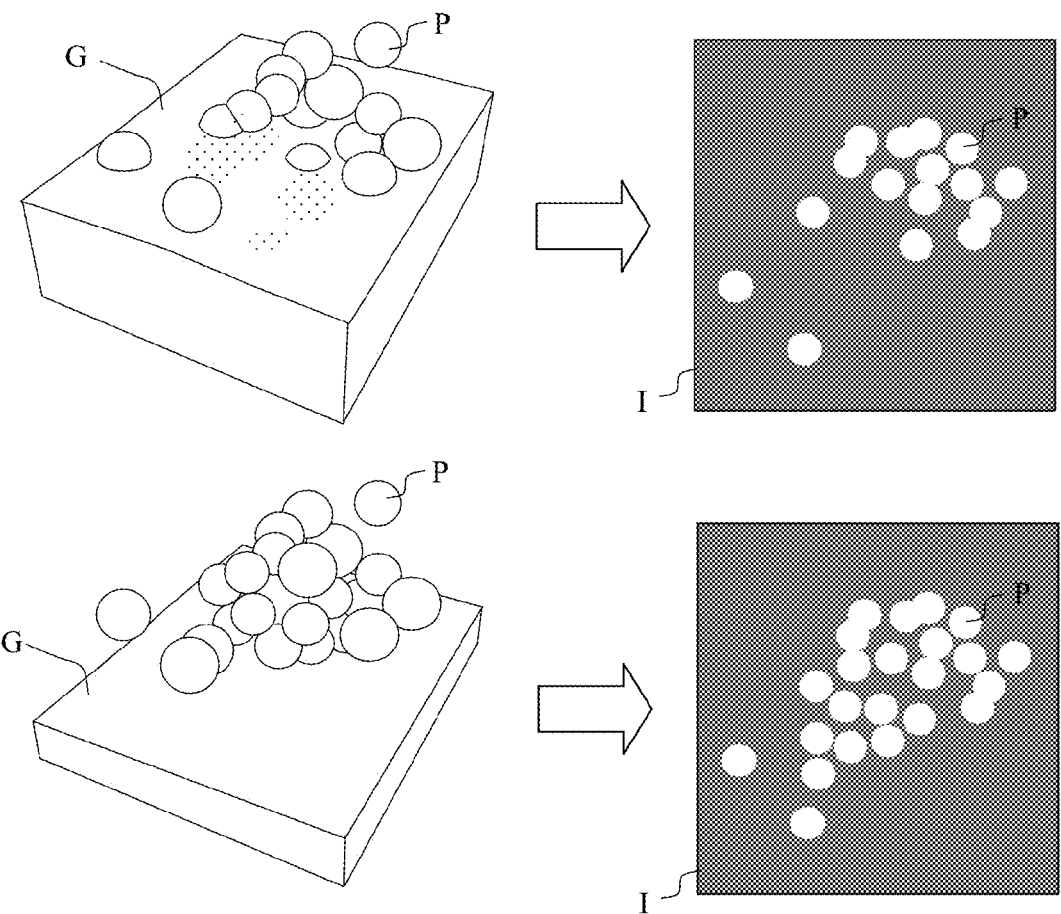
FIG. 5 shows successive detection steps implementing the process according to the invention.

Under certain conditions it is possible that, when the droplet evaporates, it is essentially the height of the droplet that decreases, the evaporation occurring from the top of the droplet toward the bottom and not from the edge of the droplet toward the center. This occurs for example when the slide is inclined by a few degrees. This effect can be used to reconstruct a three-dimensional distribution of the particles or organisms in the initial unevaporated droplet. To achieve this, it is enough to carry out a succession of detection steps at regular time intervals while the droplet is evaporating. Each detection step allows the distribution of particles or organisms in a given plane to be measured, said plane being a distance from the matrix of photosites that depends on the evaporation time, the combination of said distributions of particles or organisms obtained allowing a three-dimensional distribution of the particles or organisms in the initial unevaporated droplet to be reconstructed. FIG. 5 illustrates this principle. In this figure, three different points in time during the evaporation of a droplet containing particles are shown: on one side a three-dimensional view of a portion of the droplet and on the other side the corresponding image taken by the matrix detector of the contact imaging device. It should be noted that the three-dimensional views are not representative of the actual dimensions of the droplets or of their distribution. At time T0, only two particles have emerged from the droplet and are identifiable in the detector image. They are represented by white circles. At time T1, after 30 seconds of evaporation, a larger number of particles have emerged from the droplet and are identifiable in the detector image. Finally, at time T2, after 45 seconds of evaporation, the evaporation is practically over: all the particles have emerged and are identifiable in the detector image. Thus, from the various successive images taken at the instants T0, T1, T2, etc. it is possible to know the three-dimensional distribution of particles within the droplet.

If it is desired to completely control the process, the evaporation may be regulated by means of infrared diodes or electric heaters or by blowing gas over the meniscus of the droplet. Heating means may also be integrated into the substrate. The substrate may for example be a quartz slide onto which a thin film of ITO (indium tin oxide) has been deposited, this film then being able to form an electrical resistance. To give orders of magnitude, depending on the size of the droplet, the liquid used and the experimental conditions, the time it takes for a droplet to evaporate is from a few seconds to a few tens of seconds, the volume of the droplet being between 1 μl and 20 μl, or even more.

Various liquids like Tris(tris(hydroxymethyl)aminomethane) or purified water may be used. Tris has the advantage of being a saline solution that allows bacteria to be preserved for a few days. It is therefore widely used as a biological buffer. It is preferable for the slide carrying the droplet not to be too hydrophobic, or even hydrophilic, as will be showed later on. The process works with various types of particle. Mention is made, by way of example, of 1-μm diameter silanol microspheres, 1-μm diameter latex microspheres and bacteria. Conclusive tests were carried out on *E. Coli* or *Bacillus subtilus* bacteria. The process works with a wide range of concentrations, from one particle per droplet up to one-hundred thousand particles per droplet.

It is of course preferable for the illumination coming from the light source to be as homogenous as possible. In other words, the surface of the meniscus is illuminated with an intensity that is substantially equal at each point. It is also preferable for the illumination to have a certain spatial coherence, that is to say for the diaphragm placed in front of the source to have small dimensions. It is possible, for example, to use a diaphragm having a diameter of 100 μm.

The image capture device is simple and inexpensive since it only comprises an electronic card for capturing digital images from the photosites of a low-cost CCD sensor, or CMOS sensor in the case of a webcam, a light-emitting diode, a diaphragm and a glass slide. The pixels or photosites of the sensor may have an average size of about two to ten microns. These sensors cost much less than high-sensitivity sensors where the pixel size is no greater than two microns. The sensors are low-cost CMOS or CCD sensors.

It is possible to improve detection by using glass slides that are "functionalized" by means of antibodies so as to isolate specific bacteria from the bacterial medium. It is then possible to detect and identify the detected bacteria, the identification being dependent on the functionalization of the slide.

Figure 1:
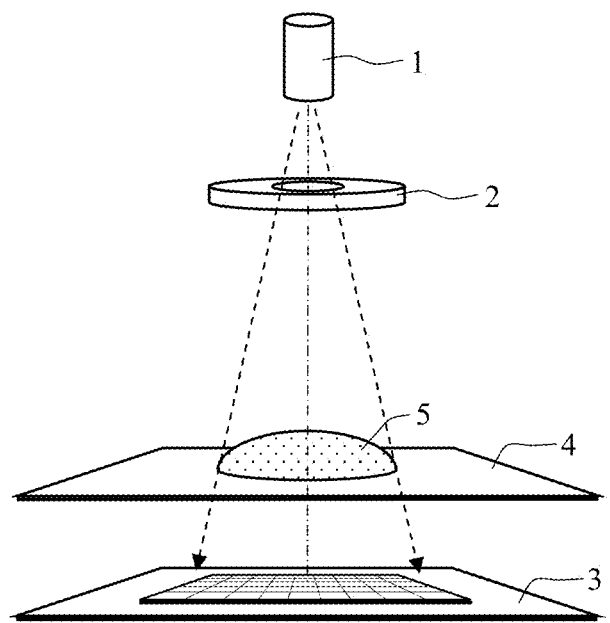
FIG. 1 shows a contact imaging device.

Detection tests were carried out using a device such as that shown in FIG. 1. The light source 1 was a 1.7 W light-emitting diode emitting at a wavelength centered on 555 nm (Luxeon® K1Luxeon III). The light source was placed 10 cm above the substrate 4. The latter was a 70 mm×25 mm×0.15 mm glass microscope slide. The sensor 3 was an 800×600 pixel CMOS image sensor having an 8-bit dynamic range. The size of each pixel was 3 μm×3 μm. This sensor was taken from a webcam (V-Gear TalkCam 2000). So as to place the substrate 4 as close as possible to the photodetector 3, the plastic membrane covering the detector was removed.

A liquid sample having a volume of approximately 1 μl was deposited on the substrate 4 opposite the sensor 3. The droplet was then allowed to evaporate over a period of a few minutes. In the experiment, the solution used was a 10 mM Tris-HCl saline solution with a pH of 8. Preferably, 0.1 vol % of polysorbate 20 (polyoxyethylene (20) sorbitan monolaurate), known by the trade name Tween 20, may be added.

FIGS. 6a, 6b and 6c show a horizontal profile PI, an image and a three-dimensional representation of said image, respectively, obtained when the sample was illuminated by a light beam made spatially coherent by placing a 100-μm diameter diaphragm between the light source and the liquid sample. In this way, it was desired to observe a diffraction pattern produced by the bacteria present in the droplet. The volume of the droplet was about 1 μl.

A holographic diffraction pattern is then observed, as described in the document by S. Su Seo "Lensless holographic imaging for on-chip cytometry and diagnostics", Lab Chip 9 (6), 777-87 (2009).

FIGS. 6d, 6e and 6f show a horizontal profile PI, an image and a three-dimensional representation of said image, respectively, obtained when the sample was illuminated by the same source but without the diaphragm. The droplet was evaporating before these images were produced. The substrate was sufficiently hydrophilic so that, while the droplet was evaporating, there remained a wetting film covering the substrate and the bacteria deposited onto the latter. This film remained all the longer because the substrate was hydrophilic and the solution of the sample was wetting and had a low surface tension—this is then referred to as ultra-wetting film formation.

The configuration implemented during the test was favored since a hydrophilic slide was used, in the present case glass that had been ultrasonically cleaned and rinsed in ethanol, and the biological buffer described above, made wetting by the addition of a wetting agent (0.1% of Tween). It was observed that, in a configuration such as that illustrated in FIG. 7, the ultra-wetting film formed, following the evaporation of the droplet, remained in place for a long time i.e. a few minutes, even a few hours.

FIGS. 6d, 6e and 6f are to be compared to FIGS. 6a, 6b and 6c, respectively. It is seen that the signal-to-noise ratio obtained from a contact image of the bacteria covered by a wetting film is increased by a factor of 20 relative to a contact image of the bacteria bathed in the droplet, thereby allowing unambiguous detection of these bacteria.

The formation of a film, resulting from the evaporation of the solution, is one of the key points of the process according to the invention. Such a film plays the role of one or more microlenses formed above the bacteria. This explains why it is possible to detect the latter with a signal-to-noise ratio that is so high, about 45.

In these examples, the signal-to-noise ratio (SNR) is defined as follows:

$$SNR = \frac{\max\{I\} - \mu}{\sigma},$$

with:
I=the amplitude measured by each pixel of the image;
μ=average amplitude of the pixels in a region considered to represent the noise; and
ρ=standard deviation of the amplitude of the pixels in a region considered to represent the noise.

When the droplet evaporates, the formation of such a film is observed on the surface of the bacteria. Depending on the solution used, and notably its wetting and surface tension properties, the film remains for a greater or lesser length of time. To estimate the thickness of this film, tests were carried out on polymer microspheres of various diameters. It was observed then that when the diameter of the microspheres was greater than 5 μm, the film systematically ruptured. Thus, it was concluded that the thickness of this film was less than a few microns, even 5 μm. The rupture of the film formed on the surface of the substrate was easily detected by producing images with the aforementioned device, schematized in FIG. 1.

Two tests were carried out using the buffer described above, one on a hydrophobic substrate the other on a hydrophilic substrate—vis-à-vis the buffer solution used. The expressions "hydrophobic" and "hydrophilic" are understood to mean that the contact angle of a droplet in contact with this substrate is greater than and less than 90°, respectively, this being a widely accepted definition.

Figure 2:
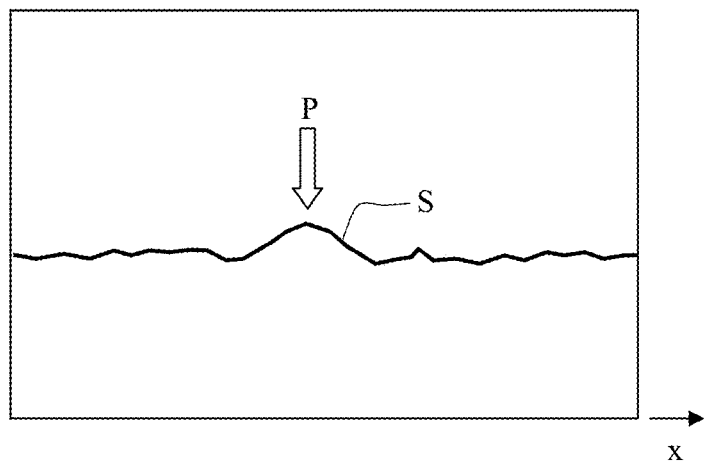
FIG. 2 shows the detection signal obtained with a low-sensitivity photosite matrix.
Figures 7A, 7B:
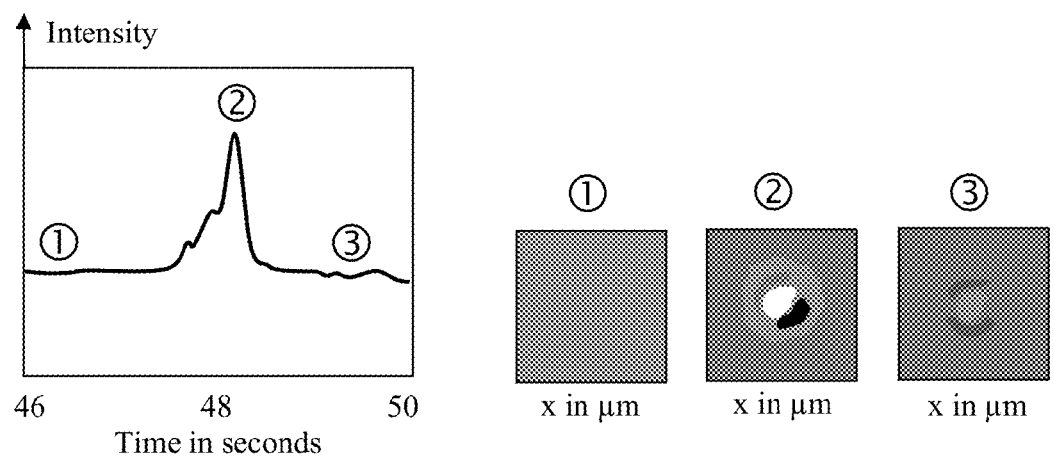
FIG. 7 shows illustrations representing observations of bacteria in a saline buffer droplet before and after evaporation, the droplet being deposited on a hydrophilic or hydrophobic slide. The curves 7a and 7c show the detected intensity as a function of time at a point located in line with the droplet.

FIGS. 7a and 7b illustrate the results obtained when the substrate is hydrophobic. FIG. 7a shows a time-course of a horizontal profile of the image of the bacteria shown in FIG. 7b, the profile passing through the center of the image of the bacteria. For t<48 s (FIG. 7b-1) the droplet evaporates and no significant signal is detected. Between t=48 s and t=49 s, the evaporation of the droplet leads to the formation of a short-lived film covering the bacteria (FIG. 7b-2). Indeed, an increase in the signal is observed, corresponding to the effect of this film forming on the bacteria. Since the substrate is hydrophobic, the film rapidly disappears, which explains the rapid decrease in the intensity of the observed signal for t>48.5 s (FIG. 7b-3).

Figures 7C, 7D:
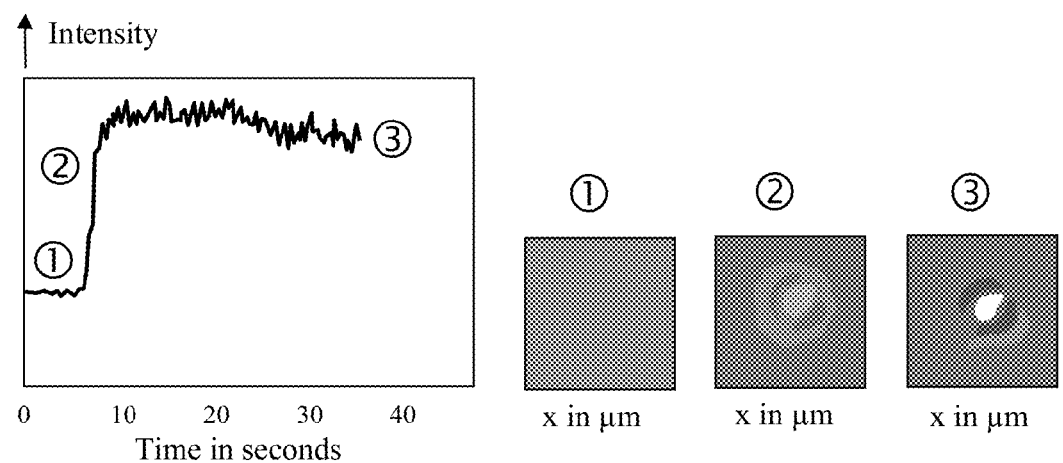

FIGS. 7c and 7d illustrate the results obtained when the substrate supporting the droplet is hydrophilic. FIG. 7c shows a time-course of a horizontal profile P of the image of the bacterium shown in FIG. 7d, the profile passing through the center of the image of the bacterium. For t<7 s, the droplet evaporates and no significant signal is detected (FIG. 7d-1). At time t=7 s the bacterium is only covered with a thin film (FIG. 7d-2). Since the substrate is hydrophilic, the film remains on the surface of the substrate and on the surface of the bacterium for a long time (FIG. 7d-3). Thus, a high-intensity signal is observed over a much longer period than in the preceding case, the period here being a few tens of seconds. After the droplet has finished evaporating, the film disappears and the bacterium is no longer detected.

These figures confirm that the process according to the invention allows a bacterium in solution to be detected at the moment when the droplet containing the bacterium evaporates, and notably when the droplet/exterior medium interface reaches the bacterium, that is to say the moment when the bacterium is only covered by a thin film. Depending on the wettability of the solution, the formation of the film is either short-lived (remaining for 1 or 2 s) or durable. The greater the wettability of the solution on the substrate considered, the more durable the formation of the film. The expression "durable" is understood to mean a film that lasts a few tens of seconds or even a few minutes or a number of hours.

Thus, when it is desired to obtain a durable film, it is preferable to add a wetting agent to the solution. Such an agent is for example Tween 20, defined above, with a concentration of 0.1 vol %.

The solution chosen for use in the tests was the buffer Tris HCl, having a Ph=8, diluted to 10 mM in distilled water—particularly satisfactory results were obtained with this buffer. Tris is the abbreviation of tris(hydroxymethyl)aminomethane or 2-amino-2-hydroxymethyl-1,3-propanediol.

Other buffers may be used. When it is desired to identify bacteria, biological buffers that keep the bacteria alive are preferred. Adding a wetting agent, such as Tween, generally proves to be very useful and allows a more durable microfilm to be formed. The volume concentration of such an agent is, for example, from about a few hundredths of a % to a few %, preferably from a few hundredths of a % to a few tens of a %. Among the other buffers that may be used, mention may be made of PBS (phosphate buffered saline) or, for nonbiological uses, distilled water.

Figure 8A:
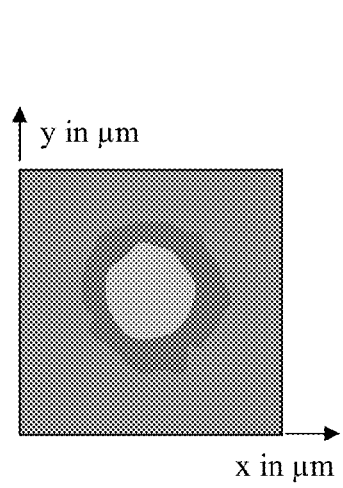
FIG. 8 shows the image of a 500-nm diameter polystyrene particle and a horizontal profile along an axis X of this image.
Figure 8B:
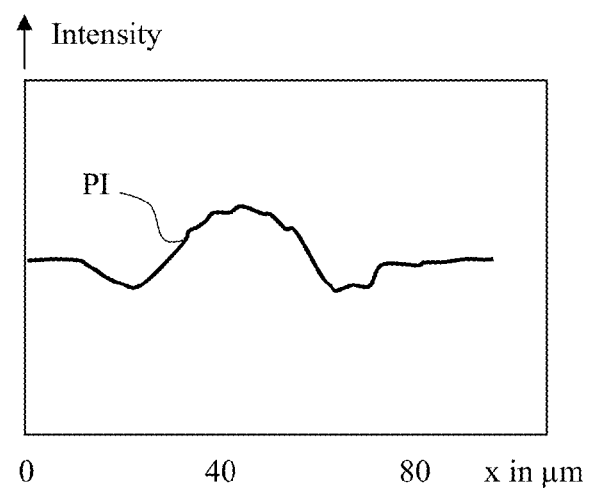

The above examples described the observation of bacteria, but the invention may be applied to the observation of particles or biological objects smaller than bacteria. FIG. 8 shows an image (FIG. 8a) and a profile PI (FIG. 8b) from the observation of a polystyrene microsphere covered with an ultra-wetting film formed subsequently to the evaporation of a droplet of the same saline buffer as that described in the above examples. The diameter of this microsphere was 500 nm. The signal-to-noise ratio detected remained high (about 20).

Moreover, by cooling the droplet holder to below the ambient temperature, the evaporation of the droplet is slowed and the residual film is more durable. For example, when the ambient temperature is 20° C. the holder may be cooled to a temperature of between 5 and 10° C.

It is then also possible to use a cooled imager, which allows the signal-to-noise ratio of the detected signal to be increased.

Concerning industrial applications of the process according to the invention, mention may be made, as nonlimiting examples, of:

monitoring air quality, in terms of bacterial and fungal content, in hospital, pharmaceutical or food-processing environments;

diagnostical measurements and diagnostic tools for preclinical studies involving microorganisms, cellular biology and pathologies; and measuring the concentrations of biological particles in body fluids.

Mention may also be made, for example, of bacterial urinary infections. Examining urine for bacteria allows urinary infection to be confirmed when a monomicrobial (single species of bacteria) bacteriuria is found with a number of bacterial colonies greater than 100 bacteria/μl, associated with a leukocyturia (presence of white blood cells in the urine) greater than 10 leukocytes/μl, or a pyuria.

Such measurements may be easily carried out with the process according to the invention.

The invention claimed is:

1. A lensfree optical imaging process for detecting micron- or submicron-sized particles or organisms by means of a contact imaging device, said particles or organisms being immersed in a liquid droplet and the detection being carried out by means of a matrix of photosensitive cells or photosites, said process comprising:
   carrying the liquid droplet on a transparent slide inserted between the matrix of photosensitive cells or photosites and a light source; and
   at least one first detection step carried out without magnifying optics while the liquid droplet is evaporating for detecting the micron- or submicron-sized particles or organisms.

2. The lensfree optical imaging process as claimed in claim 1, wherein said process comprises at least one second detection step carried out after the liquid droplet has evaporated.

3. The lensfree optical imaging process as claimed in claim 1, wherein the first detection step is carried out on a periphery of the liquid droplet, at an interface separating the liquid droplet from its evaporated part.

4. The lensfree optical imaging process as claimed in claim 1, wherein said process comprises a succession of detection steps carried out at regular time intervals while the liquid droplet is evaporating.

5. The lensfree optical imaging process as claimed in claim 4, wherein each detection step allows a distribution of particles or organisms found in a given plane to be measured, said plane being at a distance from the matrix of photosites that depends on an evaporation time, the combination of said distributions of particles or organisms obtained allowing a three-dimensional distribution of the particles or organisms in the initial unevaporated liquid droplet to be reconstructed.

6. The lensfree optical imaging process as claimed in claim 1, wherein the liquid droplet is water or a biological buffer.

7. The lensfree optical imaging process as claimed in claim 6, wherein the biological buffer is tris(hydroxymethyl)aminomethane.

8. The lensfree optical imaging process as claimed in claim 6, wherein the liquid droplet is wetted by adding a wetting agent.

9. The lensfree optical imaging process as claimed in claim 8, wherein the volume concentration of the wetting agent in the liquid droplet is between a few hundredths of a percent and a few percent.

10. The lensfree optical imaging process as claimed in claim 1, the droplet resting on the transparent slide or on a surface of the sensor.

11. The lensfree optical imaging process as claimed in claim 1, wherein the transparent slide carrying the liquid droplet is functionalized.

12. The lensfree optical imaging process as claimed in claim 10, the liquid droplet is resting on a holder cooled relative to an ambient temperature.

13. The lensfree optical imaging process as claimed in claim 11, the liquid droplet is resting on a holder cooled relative to the ambient temperature.

14. The lensfree optical imaging process as claimed in claim 1, wherein a distance separating the liquid droplet from a surface of the matrix of photosensitive cells or photosites is between 0.1 mm and 2 mm.

* * * * *

UNITED STATES PATENT AND TRADEMARK OFFICE
CERTIFICATE OF CORRECTION

| | | |
|---|---|---|
| PATENT NO. | : 8,605,265 B2 | Page 1 of 1 |
| APPLICATION NO. | : 12/994460 | |
| DATED | : December 10, 2013 | |
| INVENTOR(S) | : Cédric Allier | |

It is certified that error appears in the above-identified patent and that said Letters Patent is hereby corrected as shown below:

On the title page please add item (30)

--(30)    Foreign Application Priority Data

October 16, 2009    (FR)................... 09 04966--

Signed and Sealed this
Twenty-second Day of April, 2014

Michelle K. Lee
*Deputy Director of the United States Patent and Trademark Office*